(12) United States Patent
Fregona et al.

(10) Patent No.: US 8,481,496 B2
(45) Date of Patent: Jul. 9, 2013

(54) GOLD (III) COMPLEXES WITH OLIGOPEPTIDES FUNCTIONALIZED WITH SULFUR DONORS AND USE THEREOF AS ANTITUMOR AGENTS

(75) Inventors: Dolores Fregona, S. Pietro Viminario (IT); Luca Ronconi, Padua (IT); Fernando Formaggio, Noventa Vicentina (IT); Q. Ping Dou, Grosse Pointe, MI (US); Donatella Aldinucci, Cordenons (IT)

(73) Assignees: Universita' Degli Studi di Padova, Padua (IT); Centro di Riferimento Oncologico, Aviano (IT); Wayne State University Board of Govenors, Detroit, MI (US)

( * ) Notice: Subject to any disclaimer, the term of this patent is extended or adjusted under 35 U.S.C. 154(b) by 0 days.

(21) Appl. No.: 13/257,684

(22) PCT Filed: Mar. 20, 2009

(86) PCT No.: PCT/EP2009/053296
§ 371 (c)(1),
(2), (4) Date: Dec. 1, 2011

(87) PCT Pub. No.: WO2010/105691
PCT Pub. Date: Sep. 23, 2010

(65) Prior Publication Data
US 2012/0101044 A1    Apr. 26, 2012

(51) Int. Cl.
*A61K 38/04*    (2006.01)
(52) U.S. Cl.
USPC .......................... 514/19.2; 514/19.3; 423/463
(58) Field of Classification Search
None
See application file for complete search history.

(56) References Cited

U.S. PATENT DOCUMENTS 5,627,263 A * 5/1997 Ruoslahti et al. ............. 530/327
2005/0192242 A1* 9/2005 Neal et al. ....................... 514/44

FOREIGN PATENT DOCUMENTS

| EP | 0 195 147 A1 | 9/1966 |
| EP | 0 191 624 A2 | 8/1986 |
| GB | 2 122 194 A | 1/1984 |

OTHER PUBLICATIONS

Giovagnini, Lorena et al "Synthesis, characterization, and comparative in vitro cytotoxicity studies of platinum (II), paladium (II) and gold (III) methylsarcosinedithiocarbamate complexes." J. Med. Chem. (2005) 48 p. 1588-1595.*
IMDM medium formulation from SigmaAlrich, http://www.sigmaaldrich.com/life-science/cell-culture/learning-center/media-formulations/iscoves.html.*
Fregona D. et al; "Pt(II) and Pd(II) derivatives of ter-butylsarcosinedithiocarbamate synthesis, chemical and biological characterization and in vitro nephrotoxicity." J. Inorg. Biochem. (2003) 93 p. 181-189.*
1999 Novabiochem catalog, p. 18-19.*
Saggioro, Daniela et al, "Gold(III)-Dithiocarbamato Complexes Induce Cancer Cell Death Triggered by Thioredoxin Redox System Inhibition and Activation of ERK Pathway", Chernsitry and Biology, vol. 14, No. 10; Oct. 26, 2007; p. 1128-1139.
Aldinucci, Donatella et al.; "Antiproliferative and apoptotic effects of two new gold(III) methylsarcosinedithiocarbamate derivatives on human acute myeloid leukemia cells in vitro"; Anti-Cancer Drugs, vol. 18, No. 3; Mar. 2007; p. 323-332.
Ronconi, Luca et al.; "Gold Dithiocarbamate Derivatives as Potential Antineoplastic Agents: Design, Spectroscopic Properties, and In Vitro Antitumor Activity"; Inorganic Chemistry; vol. 44, No. 6; Mar. 21, 2005; p. 1867-1881.
Ronconi, Luca et al.; "Gold(III) Dithiocarbamate Derivatives for the Treatment of Cancer: Solution Chemistry, DNA Binding and Hemolytic Properties"; Journal of Medicinal Chemistry; vol. 49, No. 5; Mar. 5, 2006; p. 1648-1657.
Giovagnini, Lorena et al.; "Synthesis, Characterization, and Comparative in Vitro Cytotoxicity Studies of Platinum(II), Palladium(II), and Gold(III) Methylsarcosinedithiocarbamate Complexes"; Journal of Medicinal Chemistry; vol. 48, No. 5; Mar. 10, 2005; p. 1588-1595.
International Search Report for PCT/EP2009/053296 dated Jul. 14, 2009.

* cited by examiner

*Primary Examiner* — Cecilia J Tsang
*Assistant Examiner* — Fred Reynolds
(74) *Attorney, Agent, or Firm* — Gifford, Krass, Sprinkle, Anderson & Citkowski, P.C.

(57) ABSTRACT

The invention concerns Au(III) complexes of the type $[Au^{III}X_2(Pdtc)]$ (X=halogen, pseudo-halogen; pdtc=peptide-/esterified peptidedithiocarbamato) which are able to both maintain the antitumor properties and the lack of nephrotoxic side-effects of the previously reported Au(III)-dithiocarbamato complexes, together with an improved bio-availability through the peptide-mediated cellular internalization. The Au(III) complexes described have shown a significant biological activity on human tumor cell lines and, thus, they can be advantageously used as antineoplastic agents. The preparation method and use for the treatment of tumor pathologies of the Au(III) complexes of the invention are further described.

10 Claims, 2 Drawing Sheets

GOLD (III) COMPLEXES WITH OLIGOPEPTIDES FUNCTIONALIZED WITH SULFUR DONORS AND USE THEREOF AS ANTITUMOR AGENTS

CROSS-REFERENCE TO RELATED APPLICATIONS

This application is the U.S. National Phase of PCT/EP2009/053296 filed Mar. 20, 2009.

FIELD OF INVENTION

The present invention relates to Au(III)-dithiocarbamato derivatives with oligopeptides, the preparation method and use for the treatment of tumor pathologies thereof.

BACKGROUND OF THE INVENTION

In mid-60s Rosenberg serendipitously discovered the anticancer properties of cisplatin (cis-dichlorodiamminoplatinum(II), cis-[Pt$^{II}$Cl$_2$(NH$_3$)$_2$]). Following the encouraging results of these studies, it was approved by the Food and Drug Administration (FDA) at the end of 1978 for the treatment of genitourinary tumors. At present, cisplatin is one of the most effective drugs used for the treatment of testicular and, in combination with other chemotherapeutic agents, of ovarian, small-cell lung, bladder, cervical, brain and breast cancer. However, all chemotherapeutic drugs have drawbacks, and cisplatin is no exception. In fact, in spite of its therapeutic success in the treatment of several types of tumors, its high effectiveness is severely hindered by some adverse side-effects such as nausea, alopecia, ototoxicity, neurotoxicity, myelosuppression, and nephrotoxicity. A second major drawback is tumor resistance, either acquired during cycles of therapy with cisplatin (occurring in patients with, for example, ovarian cancer) or intrinsic (observed in patients with, for example, colorectal, prostate, lung or breast cancer) [L. Kelland, Nat. Rev. Cancer 2007, 7, 573-584]. Thus, much of the early effort in the design of new platinum drugs was aimed at making cisplatin-based therapy safer to patients, in particular, lessening or removing unpredictable and severe side-effects, providing oral bioavailability, and overcoming both intrinsic and acquired resistance. Efforts to mitigate the drawbacks have prompted chemists to synthesize a variety of analogues, but only a handful of new drugs were shown to be suitable for clinical application, amongst which carboplatin (cis-(1,1-cyclobutanedicarboxylato)diamminoplatinum(II)), oxaliplatin (eyhanedithioato-O,O')(R,R)-1,2-diaminocyclohexano-N,N)platinum(II)), and satraplatin (cis,trans, cis-dichlorobis(acetate-O)amino(cyclhexylamino)platinum (IV)).

Carboplatin is essentially devoid of nephrotoxicity, less neurotoxic, and less toxic to the gastrointestinal tract. By contrast, myelosuppression, principally thrombocytopenia, is its dose-limiting factor. Oxaliplatin is especially interesting for tumors which do not or hardly respond to cisplatin, for instance colorectal tumors. Nevertheless, neurotoxicity was proved to be its major drawback. Satraplatin, a Pt(IV) compound which is reduced in vivo to some Pt(II) analogues, was proved promising in terms of treatment regime since it can be administered without hospitalization.

As previously stated, kidney toxicity limits the use of cisplatin and related platinum-based therapeutics. Nephrotoxicity may result from either too high administered doses or accumulation of cisplatin in the body. The effects of cisplatin on renal functions are not completely understood, but recent research has provided new insights on the mechanism of cisplatin nephrotoxicity, especially on the signaling pathways leading to tubular cell death and inflammation. It has been hypothesized that renal failure may be induced by platinum binding to and inactivation of thiol-containing enzymes [N. Pabla, Z. Dong, Kidney Int 2008, 73, 994-1007]. Thus, a number of thiol-based and sulfur-containing nucleophiles have been tested as chemoprotectants to modulate cisplatin nephrotoxicity [R. T. Dorr, "A review of the modulation of cisplatin toxicities by chemoprotectants" in: H. M. Pinedo, J. H. Schornagel (Eds.), Platinum and Other Metal Coordination Compounds in Cancer Chemotherapy 2, Plenum Press, New York, 1996, pp. 131-154]. Two main issues have to take into account for the development of chemoprotectants: (i) the selective protection of non-tumor normal tissues, and (ii) the addition of little, if any, toxicity. Many sulfur-based chemoprotectants such as L-BSO (L-buthionine sulfoximine), disulfiram (or antabuse, tetraethylthiuram disulfide), NAC (N-acetylcysteine), mesna (S-mercaptoethane sulfonate sodium salt), sodium thiosulfate, and ORG-2766 (a melanocortin-derived peptide) have been tested to modulate cisplatin renal toxicity, and several showed promising for clinical use. However, a selective protection of normal tissues without inhibition of antitumor effects has proved challenging.

In this regard, positive outcomes were obtained with sodium diethyldithiocarbamate (DEDTNa, Na((CH$_3$CH$_2$)$_2$NCSS)). In fact, it was shown to provide protection against renal, gastrointestinal and bone marrow toxicity induced by cisplatin without decreasing its antitumor property. Its chemoprotective effect results from the capability to remove platinum from thiol groups of proteins without reversal of platinum-DNA adducts, responsible for its antitumor activity. Platinum-DNA adducts were shown to decrease by ca. 50% when cells were treated with DEDTNa soon after cisplatin administration, thus causing a loss of therapeutic effect, whereas no change in anticancer activity was observed when DEDTNa was administered 3 h after cisplatin.

However, the overall nephroprotective benefits of DEDTNa are significantly limited by the acute toxicity profile of dithiocarbamates themselves. In fact, potential human health hazards associated with free (i.e. not coordinated) dithiocarbamates is still being investigated, including genotoxicity and possible carcinogenicity [R. T. Dorr et al. 1996, ref. cit.].

Nevertheless, the wide success of platinum drugs promoted the development of both alternative platinum and other metal-based compounds that, at least in principle, might resemble its anticancer behavior.

Based on these assumptions, Faraglia G. and co-workers [G. Faraglia, D. Fregona, S. Sitran, L. Giovagnini, C. Marzano, F. Baccichetti, U. Casellato, R. Graziani, J. Inorg. Biochem. 2001, 83, 31-40] have previously designed mixed dithiocarbamato/amino Pt(II) and Pd(II) complexes ([M$^{II}$(μ-Cl)(ESDT)]$_2$, M=Pt and Pd, ESDT=CH$_3$CH$_2$O(O)CCH$_2$N(CH$_3$)CSS; [M$^{II}$Cl(ESDT)(py)], M=Pt and Pd, ESDT=CH$_3$CH$_2$O(O)CCH$_2$N(CH$_3$)CSS, py=pyridine; [M$^{II}$Cl(ESDT)(n-pra)], M=Pd, ESDT=CH$_3$CH$_2$O(O)CCH$_2$N(CH$_3$)CSS, n-pra=n-propylamine; [M$^{II}$Cl(ESDT)(en)]Cl, M=Pt and Pd, ESDT=CH$_3$CH$_2$O(O)CCH$_2$N(CH$_3$)CSS, en=ethylenediamine; [M$^{II}$Cl(ESDT)(n-pra)$_2$]Cl, M=Pd, ESDT=CH$_3$CH$_2$O(O)CCH$_2$N(CH$_3$)CSS, n-pra=n-propylamine) potentially able to combine the cytotoxic activity of the metal centers with lack of nephrotoxicity. These species contain: (i) an amino ligand as most bioactive Pt(II) complexes, (ii) a good leaving group (chloride) which may undergo hydrolysis and bind DNA, thus resembling cisplatin mechanism of action, and (iii) an S,S'-chelating ligand (dithiocarbamate) potentially able to prevent interactions of the metal centre with sulfur-containing proteins, therefore reducing renal toxicity.

These complexes were evaluated for their in vitro cytotoxic activity toward human squamous cervical adenocarcinoma (HeLa) and human leukemic promyelocites (HL60) cells. Since complex [Pt$^{II}$Cl(ESDT)(py)] showed the most promising cytotoxic properties, it was also evaluated on cisplatin-sensitive (2008) and—resistant (C13*) human ovarian carcinoma cells [C. Marzano, D. Fregona, F. Baccichetti, A. Trevisan, L. Giovagnini, F. Bordin, Chem. Biol. Interact. 2002, 140, 215-229]. Intriguingly, it induced a greater inhibition of tumor cell growth than cisplatin, and a complete lack of cross-resistance in C13* cells was observed. In addition, it was proved to be less efficient to platinate DNA, suggesting that its cytotoxic activity and the ability to overcome cisplatin resistance might be related to a different mechanism of interaction with DNA and/or with other key cellular components [C. Marzano et al. 2002, ref. cit.]. Finally, experimental results confirmed that [Pt$^{II}$Cl(ESDT)(py)] was able to induce five-fold lower renal toxicity than cisplatin [C. Marzano, A. Trevisan, L. Giovagnini, D. Fregona, Toxicol. in Vitro 2002, 16, 413-419].

Despite these encouraging results, further evaluation of [Pt$^{II}$Cl(ESDT)(py)] as potential anticancer agent was dismissed due to its poor water solubility and relatively low stability under physiological conditions. Fregona D. and co-workers carried out further studies on a number of analogous mixed dithiocarbamato/amino Pt(II) and Pd(II) complexes that exhibited high in vitro cytotoxicity together with low or even lack of nephrotoxicity [V. Alverdi, L. Giovagnini, C. Marzano, R. Seraglia, F. Bettio, S. Sitran, R. Graziani, D. Fregona, J. Inorg. Biochem. 2004, 98, 1117-1128], but long synthetic routes and inadequate stability in physiological environment was the major drawback.

In order to overcome these issues, Fregona D. and co-workers have recently explored alternative solutions, the most promising being the design of dithiocarbamato derivatives of metals other than platinum and palladium, such as Cu(II), Zn(II), and Ru(III) [L. Giovagnini, S. Sitran, M. Montopoli, L. Caparrotta, M. Corsini, C. Rosani, P. Zanello, Q. P. Dou, D. Fregona, Inorg. Chem. 2008, 47, 6336-6343; L. Giovagnini, S. Sitran, I. Castagliuolo, P. Brun, M. Corsini, P. Zanello, A. Zoleo, A. Maniero, B. Biondi, D. Fregona, Dalton Trans. 2008, 6699-6708].

In this context, Au(III) compounds are emerging as a new class of metal complexes with outstanding cytotoxic properties and are currently being evaluated as potential antitumor agents. Given their traditional use in medicine in the treatment of rheumatoid arthritis, gold compounds are a possible alternative to platinum drugs. In fact, their antiarthritic activity arises from the known immunosuppressive and antiinflammatory actions, thus establishing a connection, at least in principle, between the two therapies. Au(III) complexes show chemical features that are very close to those of clinically employed Pt(II) complexes, such as the preference for square-planar coordination and the typical $d^8$ electronic configuration, making them very attractive for testing as antineoplastic drugs. Surprisingly, despite this strict similarity, little literature data exist on the use of Au(III) complexes as anticancer agents, the paucity of data probably deriving from their high redox potential and relatively poor stability, which make their use rather problematic under physiological conditions. Recently, Fregona D. et al. have reported on some Au(III)-dithiocarbamato derivatives of the type [Au$^{III}$X$_2$(dtc)] (X=Cl, Br; dtc=various dithiocarbamato ligands: MSDT=CH$_3$O(O)CCH$_2$N(CH$_3$)CSS; ESDT=CH$_3$CH$_2$O(O)CCH$_2$N(CH$_3$)CSS; DMDT=(CH$_3$)$_2$NCSS), which have been designed in such a way to reproduce very closely the main features of cisplatin. From comparative in vitro cytotoxicity studies of Pt(II)-, Pd(II)-, and Au(III)-MSDT (MSDT=CH$_3$O (O)CCH$_2$N(CH$_3$)CSS) derivatives on human squamous cervical adenocarcinoma (HeLa) and human leukemic promyelocites (HL60) cells, Au(III) complexes resulted to be significantly more active than both cisplatin and the Pt(II) and Pd(II) counter-parts under the same experimental conditions [L. Giovagnini, L. Ronconi, D. Aldinucci, D. Lorenzon, S. Sitran, D. Fregona, J. Med. Chem. 2005, 48, 1588-1595]. [Au$^{III}$X$_2$(MSDT)]-type compounds were proved to suppress, in a dose-dependent way, cell growth on a panel of acute myelogenous leukemia cell lines with IC$_{50}$ values ca. 10-fold lower than the reference drug by inducing DNA fragmentation and cell apoptosis [D. Aldinucci, D. Lorenzon, L. Stefani, L. Giovagnini, A. Colombatti, D. Fregona, Anti-Cancer Drugs 2007, 18, 323-332]. On account of these encouraging results, Fregona D. and co-workers carried on the same way by developing other Au(III)-dithiocarbamato derivatives of the type [Au$^{III}$X$_2$(DMDT)] and [Au$^{III}$X$_2$(ESDT)] (X=Cl, Br; DMDT=(CH$_3$)$_2$NCSS; ESDT=CH$_3$CH$_2$O(O)CCH$_2$N(CH$_3$) CSS). These compounds were proved to be much more cytotoxic in vitro than cisplatin even towards human tumor cell lines intrinsically resistant to cisplatin itself. Moreover, they appeared to be much more active also on cisplatin-resistant cell lines, with activity levels comparable to those on the corresponding cisplatin-sensitive cell lines, ruling out the occurrence of cross-resistance phenomena [L. Ronconi, L. Giovagnini, C. Marzano, F. Bettio, R. Graziani, G. Pilloni, D. Fregona, Inorg. Chem. 2005, 44, 1867-1881].

Their behavior under physiological conditions and DNA binding properties have been also evaluated [L. Ronconi, C. Marzano, P. Zanello, M. Corsini, G. Miolo, C. Macca, A. Trevisan, D. Fregona, J. Med. Chem. 2006, 49, 1648-1657]. These Au(III) complexes showed high reactivity toward some biologically-relevant isolated macromolecules, resulting in a dramatic inhibition of both DNA and RNA synthesis and inducing DNA lesions with faster kinetics than cisplatin, supporting the hypothesis of a different mechanism of action compared to platinum drugs.

In this regard, the same research group have recently identified the proteasome as a major in vitro and in vivo target for these Au(III)-dithiocarbamato derivatives [V. Milacic, D. Chen, L. Ronconi, K. R. Landis-Piwowar, D. Fregona, Q. P. Dou, Cancer Res. 2006, 66, 10478-10486]. In particular, the authors showed that the inhibition of the proteasomal activity (especially, chymotrypsin-like activity) by [Au$^{III}$Br$_2$(DMDT)] is a strong apoptotic stimulus in the highly metastatic MDA-MB-231 breast cancer cell cultures and tumors. Fregona D. et al. also showed that treatment of MDA-MB-231 tumor-bearing nude mice with compound [Au$^{III}$Br$_2$(DMDT)] resulted in significant inhibition of tumor growth, as a consequence of proteasomal inhibition and apoptosis induction, together with lack of systemic toxicity, weight loss, decreased activity, or anorexia.

Saggioro D. et al. have extended the biological evaluation to mitochondria as potential target of complexes [Au$^{III}$Cl$_2$(DMDT)], [Au$^{III}$Br$_2$(DMDT)], [Au$^{III}$Cl$_2$(ESDT)] and [Au$^{II}$-$Br_2$(ESDT)] and found that they induce cancer cell death through both apoptotic and non-apoptotic mechanisms [D. Saggioro, M. P. Rigobello, L. Paloschi, A. Folda, S. A. Moggach, S. Parsons, L. Ronconi, D. Fregona, A. Bindoli, Chem. Biol. 2007, 14, 1128-1139]. They also inhibit thioredoxin reductase activity, generate free radicals, modify some mitochondrial functions, and increase ERK1/2 phosphorylation. In vivo antitumor activity as well as tolerability and nephrotoxicity of [Au$^{III}$Br$_2$(ESDT)] have been evaluated and promising results were obtained. Thus, considering the potential advantages in terms of noticeable in vitro and in vivo antitumor activity, lack of cross-resistance with cisplatin and reduced adverse side-effects, this kind of Au(III)-dithiocarbamato derivatives may be regarded as prospective metal-based anticancer drugs [V. Milacic, D. Fregona, Q. P. Dou, *Histol. Histopathol.* 2008, 23, 101-108].

Notwithstanding these positive achieved outcomes, improvement of the therapeutic efficiency of this class of complexes is still an issue as far as the crossing of cell membrane is concerned.

Actually, cellular uptake of therapeutic agents is still a challenging task because of the plasma membrane, which constitutes an impermeable barrier for most of these molecules. In order to circumvent this issue, several carrier-mediated delivery systems have been developed. Among them, much attention has recently given to the use of peptide-based delivery systems. Peptide transporters are integral plasma membrane proteins that mediate the cellular uptake of di- and tri-peptides, and peptide-like drugs [A. Biegel, S. Gebauera, B. Hartrodta, I. Knütter, K. Neuberta, M. Brandschb, I. Thondorf, *Eur. J. Pharm. Sci.* 2007, 32, 69-76]. Two peptide transporters, namely PEPT1 and PEPT2, have been identified in mammals [Rubio-Aliaga, H. Daniel *Trends Pharmacol. Sci.* 2002, 23, 434-440]. They are present predominantly in epithelial cells of the small intestine, mammary glands, lung, choroid plexus and kidney, but are also found in other cell types. A unique feature is their capability for sequence-independent transport of all possible di- and tri-peptides, including differently charged species. These transporters are stereoselective toward peptides containing L-enantiomers of amino acids. Both PEPT1 and PEPT2 exhibit a similar substrate specificity but differ in structure, transport capacity, and binding affinity. PEPT1 is a low-affinity, high-capacity transporter, whereas PEPT2 acts with high affinity and low capacity. Thus, peptide transporters represent excellent targets for the delivery of pharmacologically active compounds because their substrate-binding site can accommodate a wide range of molecules of different size, hydrophobicity and charge.

Metal complexes of peptides have been widely used as models for the interaction between metal ions and proteins, most of these studies concerning Pt(II). Nevertheless, only a few Pt(II)-peptido complexes have been isolated, the major drawback being their kinetic inertness, and only very few studies concerning Au(III)-peptido derivatives with the avowed aim of investigating the direct interaction between Au$^{3+}$ ion and biomolecules have been reported [M. Wienken, B. Lippert, E. Zangrando, L. Randaccio *Inorg. Chem.* 1992, 31, 1983-1985; S. Carotti, G. Marcon, M. Marussich, T. Mazzei, L. Messori, E. Mini, P. Orioli, *Chem. Biol. Interact.* 2000, 125, 29-38].

SUMMARY OF THE INVENTION

The purpose of the present invention is to provide Au(III) complexes characterized by suitable antitumor properties and lack of toxicity (in particular nephrotoxicity), and showing improved intracellular drug transfer and delivery.

Furthermore, another aim of the present invention is to provide Au(III) complexes that, together with the above mentioned suitable biological properties, might be easily obtainable and sufficiently stable, making their synthetic process profitable in bulk at industrial level.

For these aims new Au(III)-dithiocarbamato derivatives of oligopeptides, as potential improved intracellular drug transfer and delivery systems supported by transporter proteins, have been identified as a possible class of compounds suitable to solve the herein above mentioned issue of cell targeting of the metal-based anticancer drugs.

Therefore, in a first aspect the present invention relates to Au(III) complexes of the type [Au$^{III}$X$_2$(pdtc)] (X=halogen, pseudo-halogen; pdtc=peptide/esterified peptidedithiocarbamato) which are able to both maintain the antitumor properties and the lack of nephrotoxic side-effects of the previously reported Au(III)-dithiocarbamato complexes, together with an improved bioavailability through the peptide-mediated cellular internalization.

The Au(III) complexes object of the present invention are Au(III)-dithiocarbamato derivatives with oligopeptides [Au$^{III}$X$_2$(pdtc)] represented by the general formula (I)

and pharmaceutically acceptable salts thereof
wherein:
X$^1$, X$^2$, equal or different each other, are selected from the group consisting of Cl, Br, I, CN, SCN;
m is an integer comprised in a range from 2 to 5;
the organic moieties [—C(=O)—Z$_n$—C(R$^2$)(R$^3$)—N(R$^1$)—] are amino acid residue equal or different each other, where R$^1$, R$^2$, R$^3$ and Z$_n$, equal or different each other, are:
R$^1$ is a residue selected from the group consisting of H, CH$_3$, straight or branched C$_2$-C$_6$ alkyl, C$_3$-C$_6$ cycloalkyl, phenyl, CH$_2$ bound to R$^3$ where R$^3$ is equal to (CH$_2$)$_2$;
R$^2$ is a residue selected from the group consisting of H, CH$_3$, straight or branched C$_2$-C$_6$ alkyl, C$_3$-C$_6$ cycloalkyl, phenyl;
R$^3$ is a residue selected from the group consisting of H, CH$_3$, CH(CH$_3$)$_2$, (CH$_2$)$_2$ bound to R$^1$ where R$^1$ is equal to CH$_2$, CH$_2$CH(CH$_3$)$_2$, CH(CH$_3$)CH$_2$CH$_3$, CH$_2$—(C$_6$H$_5$), CH$_2$OH, CH$_2$—(C$_6$H$_4$)—OH, CH(CH$_3$)OH, CH$_2$SH, (CH$_2$)$_2$C(=O)NH$_2$, (CH$_2$)$_3$NHC(=NH)NH$_2$, (CH$_2$)$_2$SCH$_3$, (CH$_2$)$_4$NH$_2$, CH$_2$C(=O)NH$_2$, CH$_2$C(=O)OH, (CH$_2$)$_2$C(=O)OH;
Z$_n$ (n=0, 1) is —C—(R$^5$)(R$^6$) where R$^5$, R$^6$, equal or different each other, are residues selected from the group consisting of H, CH$_3$, straight or branched C$_2$-C$_6$ alkyl, C$_3$-C$_6$ cycloalkyl, phenyl;
Y is selected from O, S, NR$^7$, where R$^7$ is a residue selected from the group consisting of H, CH$_3$, straight or branched C$_2$-C$_6$ alkyl, C$_3$-C$_6$ cycloalkyl, phenyl;

$R^4$ is a residue selected from the group consisting of H, $CH_3$, straight or branched $C_2$-$C_6$ alkyl, $C_3$-$C_6$ cycloalkyl, phenyl, $(CH_2CH_2O)_p$H where p is an integer comprised from 1 to 4.

The present invention further extends to the [Au$^{III}$X$_2$(pdtc)] complexes represented by the general formula (I) wherein:
the chiral carbon atom bound to $R^2$ and $R^3$ has R stereochemistry;
the chiral carbon atom bound to $R^2$ and $R^3$ has S stereochemistry;
the chiral carbon atom bound to $R^5$ and $R^6$ has R stereochemistry;
the chiral carbon atom bound to $R^5$ and $R_6$ has S stereochemistry; and to pharmaceutically acceptable salts thereof.

Further objects of the invention are the whole synthetic process leading to the formation of the [Au$^{III}$X$_2$(pdtc)] complexes of general formula (I) and use as antineoplastic agents for the treatment of tumor pathologies thereof.

The aims and benefits of the new Au(III)-dithiocarbamato derivatives of oligopeptides [Au$^{III}$X$_2$(pdtc)] complexes as antineoplastic agents, object of the present invention, will be better understood while going through the following detailed description.

DETAILED DESCRIPTION OF THE INVENTION

The enormous potential impact on the existing therapeutic need to have novel and more selective metal-based chemotherapeutic agents, with a possible site-specific delivery in localized cancers, has prompted the inventors to design new Au(III) complexes trying to strongly improve their cellular uptake and to minimize unwanted side-effects typical of the metal-based chemotherapeutic agents.

Thus, the [Au$^{III}$X$_2$(pdtc)] complexes represented by the general formula (I) herein previously reported were designed in the attempt to reproduce very closely the main features of the reference drug cisplatin, and to improve the cellular uptake by using peptides (combined with the presence of a dithiocarbamato moiety as intrinsic chemoprotectant) directly bound to the Au(III) metal center as carriers for an enhanced intracellular delivery of the drug.

In fact, these complexes should exhibit an almost square-planar geometry and contain two cis-Au(III)-halogen or pseudo-halogen bonds that may undergo easy hydrolysis, the remaining coordination positions being occupied by a peptide-dithiocarbamato ligand, the —NCSS moiety coordinating the metal center through the sulfur donating atoms in a bidentate symmetrical mode and lying in the same plane.

However, gold exhibits different oxidation states and has rich coordination chemistry. Thus, as well known for this kind of metals and for gold in particular, even little changes in its complexes can result in dramatic changes in their physico-chemical properties and, therefore, in their biological properties. Thus, moving from the previously reported Au(III) analogues containing a single amino acid dithiocarbamato ligand [L. Ronconi et al. 2005, ref. cit.] to the compounds object of the present invention a change in their chemical and biological behavior might have been expected. In fact, prolongation of the amino acid chain of the dithiocarbamato ligand might have led (and, for future compounds, might actually lead) to dramatic changes in their properties, such as stability under physiological conditions, antitumor activity, nephrotoxicity and cross-resistance, whose prediction is not trivial at all.

In a first embodiment of the invention the oligopeptide moiety of the ligand pdtc is a dithiocarbamato derivative of a peptide/esterified peptide consisting of 2 to 5 amino acids, either natural or synthetic showing, independently each other, S (L) or R (D) stereochemistry. Preferably, the amino acids are selected in the group consisting of glycine (Gly), alanine (Ala), proline (Pro), serine (Ser), sarcosine (Sar), α-aminoisobutyric (Aib), phenylalanine (Phe).

In the more preferred embodiments of the Au(III) complexes according to the general formula (I):
$X^1$ and $X^2$ are halogens selected from Cl and Br;
the oligopeptide residue of the ligand pdtc is selected from the group consisting of -Sar-Gly-, -Sar-Aib-, -Sar-Phe-, -Sar-Ser- -Sar-Aib$_2$-, -Sar-Aib$_3$-Gly-;
Y is O;
$R^4$ is selected from the group consisting of methyl, ethyl, t-butyl.

As a most preferred embodiment the pdtc ligand is selected from the group consisting of (t-Bu)O-Gly-Sar-CSS, (t-Bu)O-Aib-Sar-CSS, (t-Bu)O-Phe-Sar-CSS, MeO-Gly-Sar-CSS, MeO-Aib-Sar-CSS, MeO-Ser-Sar-CSS, MeO-Phe-Sar-CSS, (t-Bu)O-Aib$_2$-Sar-CSS$^-$, EtO-Gly-Aib$_3$-Sar-CSS.

The complexes according to the invention have shown a relevant in vitro cytotoxicity, associated to a capacity to induce apoptosis on human cancer cell lines, both effects significantly higher than the reference drug cisplatin. In addition, these complexes were capable to inhibit the proteasomal chymotrypsin-like activity on purified proteosome and on a whole tumor cell line extract, resulting two-fold more potent than the previously investigated Au(III)-dithiocarbamato analogues.

Therefore, the Au(III) complexes of the invention can be usefully employed as antineoplastic agents for the treatment of tumor pathologies. In particular, the Au(III) complexes herein disclosed can be used on their own or in combination with other chemotherapeutic agents to treat neoplastic pathologies such as lymphomas, myelomas, acute and chronic leukemia, genitourinary, testicular and ovarian, small-cell lung, bladder, cervical, brain and breast cancer.

For this purpose the complexes can be used for the preparation of compositions in combination with pharmaceutically acceptable excipients and/or diluents suitable for parenteral, oral, local and transdermical administration. The compositions can be fast- or slow-release compositions ready for treatment or prepared at the time of administration. The compositions comprising the Au(III) complexes of the general formula (I) can be also administered by means of suitable device for general and local administration.

The general synthetic process leading to the complexes of the type [Au$^{III}$X$_2$(pdtc)] (X=halogen, pseudo-halogen; pdtc=peptide-/esterified peptidedithiocarbamato) according to the invention may be summarized as follows steps by steps:

1) in situ template synthesis of the dithiocarbamato ligand by a 1:1:1 stoichiometric reaction between a selected peptide/esterified peptide hydrochloride (p.HCl), carbon disulfide (CS$_2$) and sodium or potassium hydroxide (MOH, M=Na, K) in water at 0° C., leading to the formation of the corresponding dithiocarbamic acid (pdtcH=p-C(S)SH), according to the reaction 2) coordination of the dithiocarbamato ligand to the gold metal center by a 2:1 ligand-to metal reaction between the dithiocarbamato ligand generated in situ (previous step 1) and M[Au$^{III}$X$_4$] (M=Na, K) in water at 0° C., leading to the precipitation of the complex [Au$^{III}$X$_2$(pdtc)], according to the reaction

3) separation and optional purification of complex [Au$^{III}$X$_2$(pdtc)].

The solid obtained at previous step 2 is separated by centrifugation, washed several times with water, and dried under reduced pressure with P$_2$O$_5$.

Some Au(III)-dithiocarbamato derivatives of oligopeptides having the general formula (I) have been synthesized, purified and fully characterized. Non-limitative examples of the synthesis of these complexes and the in vitro antitumor activity thereof will be described herein below.

Synthesis and Characterization of [Au$^{III}$X$_2$(pdtc)] Complexes

The eight esterified peptides (P1-P9) below reported have been synthesized as hydrochlorides following well-established procedures previously reported in the literature [G. M. Bonora, C. Toniolo, Biopolymers 1974, 13, 2179-2190; M. K. Dhaon, R. K. Olsen, K. Ramasamy, *J. Org. Chem.* 1982, 47, 1962-1965; D. S. Jones, G. W. Kenner, J. Preston, R. C. Sheppard, *J. Chem. Soc.* 1965, 6227-6239], purified and fully characterized. When present, chiral amino acids have S (L) stereochemistry.

R = CH$_3$, HCl•H-Sar-Gly-OMe (P1)
R = C(CH$_3$)$_3$, HCl•H-Sar-Gly-O(t-Bu) (P2)

R = CH$_3$, HCl•H-Sar-Aib-OMe (P3)
R = C(CH$_3$)$_3$, HCl•H-Sar-Aib-O(t-Bu) (P4)

R = CH$_3$, HCl•H-Sar-Phe-OMe (P5)
R = C(CH$_3$)$_3$, HCl•H-Sar-Phe-O(t-Bu) (P6)

HCl•H-Sar-Aib$_2$-O(t-Bu) (P7)

HCl•H-Sar-Aib$_3$-Gly-OEt (P8)

HCl•H-Sar-Ser-OMe (P9)

wherein Sar=sarcosine; Gly=glycine; Aib=α-aminoisobutyric; Phe=phenylalanine; Ser=serine.

Then, these oligopeptides were used for the synthesis and characterization of the Au(III)-dithiocarbamato derivatives of oligopeptides herein below reported both as chemical structures and synthesis

X = Br, [Au^III Br2((t-Bu)O-Gly-Sar-dtc)] (AUD6)
X = Cl, [Au^III Cl2((t-Bu)O-Gly-Sar-dtc)] (AUD7)

X = Br, [Au^III Br2((t-Bu)O-Aib-Sar-dtc)] (AUD8)
X = Cl, [Au^III Cl2((t-Bu)O-Aib-Sar-dtc)] (AUD9)

X = Br, [Au^III Br2((t-Bu)O-Phe-Sar-dtc)] (AUD10)
X = Cl, [Au^III Cl2((t-Bu)O-Phe-Sar-dtc)] (AUD11)

[Au^III Br2(EtO-Gly-Aib3-Sar-dtc)] (AUD12)

X = Br, [Au^III Br2((t-Bu)O-Aib2-Sar-dtc)] (AUD13)
X = Cl, [Au^III Cl2((t-Bu)O-Aib2-Sar-dtc)] (AUD14)

wherein Sar=sarcosine; Gly=glycine; Aib=α-aminoisobutyric; Phe=phenylalanine.

Example 1

[Au^III Br2((t-Bu)O-Gly-Sar-dtc)] (AUD6)

A water solution (ca. 3 mL) of HCl.H-Sar-Gly-O(t-Bu) (1.42 mmol) cooled at 0° C. was drop-wise treated under continuous stirring with cool $CS_2$ (1.43 mmol) and an aqueous solution (1 mL) of NaOH (1.42 mmol). When pH turned from 11 to 6 after ca. 2 h, the solution was slowly added under stirring to an aqueous cool (0° C.) solution (ca. 2 mL) of K[AuBr$_4$] (0.70 mmol), leading to the immediate precipitation of a reddish-brown solid that was filtered off, washed with water, and dried under reduced pressure with $P_2O_5$, the final yield being 77.2%.

Elemental analyses calculated for $C_{10}H_{17}AuBr_2N_2O_3S_2$: C, 18.94; H, 2.70; N, 4.42; S, 10.11%. Found: C, 19.20; H, 2.88; N, 4.42; S, 10.25%.

Melting point: the complex decomposes at 152.6° C.

IR data (KBr, cm$^{-1}$): 3352 (v, N—H); 1736 (v, C=O ester); 1673 (v, C=O amide); 1568 (v, amide II+N—CSS); 1253 (v, amide III); 1228 (v, C—O(t-Bu)); 1161 (v, (t-Bu)—O); 1006, 556 ($v_{a,s}$, S—C—S); 387 ($v_{a,s}$, S—Au—S); 252, 227 ($v_{a,s}$, Br—Au—Br).

$^1$H NMR (300.13 MHz, acetone-D$_6$, 298 K): δ (ppm) 1.45 (C(CH$_3$)$_3$); 3.53, 3.57 (NCH$_3$); 3.95, 3.96 (CH$_2$ Gly); 4.71, 4.75 (CH$_2$ Sar); 7.96 (NH).

$^{13}$C NMR (75.48 MHz, acetone-D$_6$, 298 K): δ (ppm) 28.66 (C(CH$_3$)$_3$); 40.13, 41.12 (NCH$_3$); 43.09 (CH$_2$ Gly); 55.12, 58.98 (CH$_2$ Sar); 82.59 (C(CH$_3$)$_3$); 165.06, 165.35 (NCO); 169.93 (COO); 196.74, 200.48 (CSS).

Example 2

[Au^III Cl2((t-Bu)O-Gly-Sar-dtc)] (AUD7)

A water solution (ca. 3 mL) of HCl.H-Sar-Gly-O(t-Bu) (1.56 mmol) cooled at 0° C. was drop-wise treated under continuous stirring with cool $CS_2$ (1.58 mmol) and an aqueous solution (1 mL) of NaOH (1.58 mmol). When pH turned from 11 to 6 after ca. 2 h, the solution was slowly added under stirring to an aqueous cool (0° C.) solution (ca. 2 mL) of K[AuCl$_4$] (0.77 mmol), leading to the immediate precipitation of a yellow-ochre solid that was filtered off, washed with water, and dried under reduced pressure with $P_2O_5$, the final yield being 76.9%.

Elemental analyses calculated for $C_{10}H_{17}AuCl_2N_2O_3S_2$: C, 22.03; H, 3.14; N, 5.14; S, 11.76%. Found: C, 22.00; H, 3.23; N, 5.08; S, 11.96%.

Melting point: the complex decomposes at 155.3° C.

IR data (KBr, cm$^{-1}$): 3349 (v, N—H); 1737 (v, C=O ester); 1672 (v, C=O amide); 1561 (v, amide II+N—CSS); 1253 (v, amide III); 1229 (v, C—O(t-Bu)); 1162 (v, (t-Bu)—O); 1006, 558 ($v_{a,s}$, S—C—S); 384 ($v_{a,s}$, S—Au—S); 358, 339 ($v_{a,s}$, Cl—Au—Cl).

$^1$H NMR (300.13 MHz, acetone-D$_6$, 298 K): δ (ppm) 1.45 (C(CH$_3$)$_3$); 3.56, 3.57 (NCH$_3$); 3.94, 3.97 (CH$_2$ Gly); 4.75 (CH$_2$ Sar); 7.92 (NH).

$^{13}$C NMR (75.48 MHz, acetone-D$_6$, 298 K): δ (ppm) 28.70 (C(CH$_3$)$_3$); 40.66, 41.10 (NCH$_3$); 43.27 (CH$_2$ Gly); 55.64 (CH$_2$ Sar); 82.66 (C(CH$_3$)$_3$); 165.10 (NCO); 169.82 (COO); 195.45, 200.60 (CSS).

Example 3

[Au$^{III}$Br$_2$((t-Bu)O-Aib-Sar-dtc)] (AUD8)

A water solution (ca. 3 mL) of HCl.H-Sar-Aib-O(t-Bu) (1.43 mmol) cooled at 0° C. was drop-wise treated under continuous stirring with cool CS$_2$ (1.43 mmol) and an aqueous solution (1 mL) of NaOH (1.42 mmol). When pH turned from 11 to 6 after ca. 2.5 h, the solution was slowly added under stirring to an aqueous cool (0° C.) solution (ca. 2 mL) of K[AuBr$_4$] (0.71 mmol), leading to the immediate precipitation of a reddish-brown solid that was filtered off, washed with water, and dried under reduced pressure with P$_2$O$_5$, the final yield being 76.4%.

Elemental analyses calculated for C$_{12}$H$_{21}$AuBr$_2$N$_2$O$_3$S$_2$: C, 21.76; H, 3.20; N, 4.23; S, 9.68%. Found: C, 22.03; H, 3.33; N, 4.34; S, 9.58%.

M.p.: decomposes at 165.9° C.

IR data (KBr, cm$^{-1}$): 3362 (ν, N—H); 1734 (ν, C=O ester); 1690 (ν, C=O amide); 1560 (ν, N—CSS); 1531 (ν, amide II); 1252 (ν, amide III); 1215 (ν, C—O(t-Bu)); 1144 (ν, (t-Bu)—O); 996, 545 (ν$_{a,s}$, S—C—S); 383 (ν$_{a,s}$, S—Au—S); 252, 223 (ν$_{a,s}$, Br—Au—Br).

$^1$H NMR (300.13 MHz, acetone-D$_6$, 298 K): δ (ppm) 1.44 (C(CH$_3$)$_3$); 1.45, 1.46 (C(CH$_3$)$_2$ Aib); 3.51, 3.54 (NCH$_3$); 4.62, 4.66 (CH$_2$ Sar); 7.90 (NH).

$^{13}$C NMR (75.48 MHz, acetone-D$_6$, 298 K): δ (ppm) 25.61 (C(CH$_3$)$_2$ Aib); 28.60 (C(CH$_3$)$_3$); 40.21, 41.20 (NCH$_3$); 55.26, 56.15 (CH$_2$ Sar); 58.35 (C(CH$_3$)$_2$ Aib); 81.91 (C(CH$_3$)$_3$); 164.00 (NCO); 173.73 (COO); 196.57, 200.26 (CSS).

Example 4

[Au$^{III}$Cl$_2$((t-Bu)O-Aib-Sar-dtc)] (AUD9)

A water solution (ca. 3 mL) of HCl.H-Sar-Aib-O(t-Bu) (1.58 mmol) cooled at 0° C. was drop-wise treated under continuous stirring with cool CS$_2$ (1.58 mmol) and an aqueous solution (1 mL) of NaOH (1.59 mmol). When pH turned from 11 to 6 after ca. 2.5 h, the solution was slowly added under stirring to an aqueous cool (0° C.) solution (ca. 2 mL) of K[AuCl$_4$] (0.78 mmol), leading to the immediate precipitation of a yellow-ochre solid that was filtered off, washed with water, and dried under reduced pressure with P$_2$O$_5$, the final yield being 80.6%.

Elemental analyses calculated for C$_{12}$H$_{21}$AuCl$_2$N$_2$O$_3$S$_2$: C, 25.14; H, 3.69; N, 4.89; S, 11.19%. Found: C, 25.11; H, 3.84; N, 4.84; S, 11.37%.

Melting point: the complex decomposes at 166.6° C.

IR data (KBr, cm$^{-1}$): 3365 (ν, N—H); 1733 (ν, C=O ester); 1691 (ν, C=O amide); 1564 (ν, N—CSS); 1534 (ν, amide II); 1252 (ν, amide III); 1214 (ν, C—O(t-Bu)); 1146 (ν, (t-Bu)—O); 996, 547 (ν$_{a,s}$, S—C—S); 383 (ν$_{a,s}$, S—Au—S); 347 (ν$_{a,s}$, Cl—Au—Cl).

$^1$H NMR (300.13 MHz, acetone-D$_6$, 298 K): δ (ppm) 1.44 (C(CH$_3$)$_3$); 1.45, 1.46 (C(CH$_3$)$_2$ Aib); 3.54, 3.55 (NCH$_3$); 4.66 (CH$_2$ Sar); 7.89 (NH).

$^{13}$C NMR (75.48 MHz, acetone-D$_6$, 298 K): δ (ppm) 25.52 (C(CH$_3$)$_2$ Aib); 28.50 (C(CH$_3$)$_3$); 40.64, 41.04 (NCH$_3$); 55.67 (CH$_2$ Sar); 58.20 (C(CH$_3$)$_2$ Aib); 81.87 (C(CH$_3$)$_3$); 163.80 (NCO); 173.62 (COO); 195.09, 200.19 (CSS).

Example 5

[Au$^{III}$Br$_2$((t-Bu)O-Phe-Sar-dtc)] (AUD10)

A water solution (ca. 3 mL) of HCl.H-Sar-Phe-O(t-Bu) (1.38 mmol) cooled at 0° C. was drop-wise treated under continuous stirring with cool CS$_2$ (1.39 mmol) and an aqueous solution (1 mL) of NaOH (1.38 mmol). When pH turned from 11 to 6 after ca. 1.5 h, the solution was slowly added under stirring to an aqueous cool (0° C.) solution (ca. 2 mL) of K[AuBr$_4$] (0.69 mmol), leading to the immediate precipitation of a reddish-brown solid that was filtered off, washed with water, and dried under reduced pressure with P$_2$O$_5$, the final yield being 71.5%.

Elemental analyses calculated for C$_{17}$H$_{23}$AuBr$_2$N$_2$O$_3$S$_2$: C, 28.19; H, 3.20; N, 3.87; S, 8.85%. Found: C, 28.34; H, 3.09; N, 3.87; S, 8.63%.

Melting point: the complex decomposes at 124.3° C.

IR data (KBr, cm$^{-1}$): 3431 (ν, N—H); 1731 (ν, C=O ester); 1683 (ν, C=O amide); 1558 (ν, N—CSS); 1543 (ν, amide II); 1259 (ν, amide III); 1214 (ν, C—O(t-Bu)); 1155 (ν, (t-Bu)—O); 994, 562 (ν$_{a,s}$, S—C—S); 381 (ν$_{a,s}$, S—Au—S); 252, 221 (ν$_{a,s}$, Br—Au—Br).

$^1$H NMR (300.13 MHz, acetone-D$_6$, 298 K): δ (ppm) 1.43 (C(CH$_3$)$_3$); 2.98-3.20 (CH$_2$-Ph); 3.45, 3.49 (NCH$_3$); 4.65, 4.70 (CH$_2$ Sar); 4.67-4.74 (CH); 7.25-7.33 (C$_6$H$_5$); 7.91 (NH).

$^{13}$C NMR (75.48 MHz, acetone-D$_6$, 298 K): δ (ppm) 28.11 (C(CH$_3$)$_3$); 38.50 (CH$_2$-Ph); 39.74, 40.74 (NCH$_3$); 54.65, 55.56 (CH$_2$ Sar); 55.23 (CH); 82.56 (C(CH$_3$)$_3$); 127.86 (Ph, p-CH); 129.41 (Ph, m-CH); 130.43 (Ph, o-CH); 137.72 (Ph, CH$_2$—C); 164.10, 164.33 (NCO); 170.75 (COO); 196.11, 199.33 (CSS).

Example 6

[Au$^{III}$Cl$_2$((t-Bu)O-Phe-Sar-dtc)] (AUD11)

A water solution (ca. 3 mL) of HCl.H-Sar-Phe-O(t-Bu) (1.62 mmol) cooled at 0° C. was drop-wise treated under continuous stirring with cool CS$_2$ (1.64 mmol) and an aqueous solution (1 mL) of NaOH (1.61 mmol). When pH turned from 11 to 6 after ca. 1.5 h, the solution was slowly added under stirring to an aqueous cool (0° C.) solution (ca. 2 mL) of K[AuCl$_4$] (0.80 mmol), leading to the immediate precipitation of a light-brown solid that was filtered off, washed with water, and dried under reduced pressure with P$_2$O$_5$, the final yield being 81.7%.

Elemental analyses calculated for C$_{17}$H$_{23}$AuCl$_2$N$_2$O$_3$S$_2$: C, 32.14; H, 3.65; N, 4.41; S, 10.09%. Found: C, 32.31; H, 3.54; N, 4.40; S, 9.95%.

Melting point: the complex decomposes at 138.3° C.

IR data (KBr, cm$^{-1}$): 3342 (ν, N—H); 1733 (ν, C=O ester); 1684 (ν, C=O amide); 1559 (ν, N—CSS); 1542 (ν, amide II); 1256 (ν, amide III); 1213 (ν, C—O(t-Bu)); 1155 (ν, (t-Bu)—O); 994, 563 (ν$_{a,s}$, S—C—S); 383 (ν$_{a,s}$, S—Au—S); 359 (ν$_{a,s}$, Cl—Au—Cl).

$^1$H NMR (300.13 MHz, acetone-D$_6$, 298 K): δ (ppm) 1.43 (C(CH$_3$)$_3$); 2.98-3.20 (CH$_2$-Ph); 3.49 (NCH$_3$); 4.70 (CH$_2$ Sar); 4.67-4.74 (CH); 7.25-7.33 (C$_6$H$_5$); 7.92 (NH).

$^{13}$C NMR (75.48 MHz, acetone-D$_6$, 298 K): δ (ppm) 27.86 (C(CH$_3$)$_3$); 38.29 (CH$_2$-Ph); 40.49 (NCH$_3$); 55.31 (CH$_2$ Sar); 54.97 (CH); 82.33 (C(CH$_3$)$_3$); 127.50 (Ph, p-CH); 129.15 (Ph, m-CH); 130.40 (Ph, o-CH); 137.73 (Ph, CH$_2$—C); 163.97, 164.10 (NCO); 170.93 (COO); 194.45, 199.61 (CSS).

Example 7

[Au$^{III}$Br$_2$(EtO-Gly-Aib$_3$-Sar-dtc)] (AUD 12)

A water solution (ca. 3 mL) of HCl.H-Sar-Aib$_3$-Gly-OEt (0.84 mmol) cooled at 0° C. was drop-wise treated under continuous stirring with cool CS$_2$ (0.86 mmol) and an aqueous solution (1 mL) of NaOH (0.84 mmol). When pH turned from 11 to 6 after ca. 2 h, the solution was slowly added under stirring to an aqueous cool (0° C.) solution (ca. 2 mL) of K[AuBr$_4$] (0.41 mmol), leading to the immediate precipitation of a reddish-brown solid that was filtered off, washed with water, and dried under reduced pressure with P$_2$O$_5$, the final yield being 78.9%.

Elemental analyses calculated for C$_{20}$H$_{34}$AuBr$_2$N$_5$O$_6$S$_2$: C, 27.89; H, 3.98; N, 8.13; S, 7.44%. Found: C, 27.71; H, 4.10; N, 8.24; S, 7.58%.

M.p.: decomposes at 160.3° C.

IR data (KBr, cm$^{-1}$): 3358 (v, N—H); 1741 (v, C=O ester); 1689 (v, C=O amide); 1563 (v, N—CSS); 1533 (v, amide II); 1253 (v, amide III); 1240 (v, C—OEt); 1098 (v, Et-O); 998, 547 (v$_{a,s}$, S—C—S); 384 (v$_{a,s}$, S—Au—S); 253, 222 (v$_{a,s}$, Br—Au—Br).

$^1$H NMR (300.13 MHz, acetone-D$_6$, 298 K): δ (ppm) 1.22 (CH$_3$ Et); 1.38-1.51 (C(CH$_3$)$_2$ Aib); 3.54, 3.58 (NCH$_3$); 3.86, 3.90 (CH$_2$ Gly); 4.10 (CH$_2$ Et); 4.80, 4.83 (CH$_2$ Sar); 7.15-8.38 (NH).

Example 8

[Au$^{III}$Br$_2$((t-Bu)O-Aib$_2$-Sar-dtc)] (AUD13)

A water solution (ca. 3 mL) of HCl.H-Sar-Aib$_2$-O(t-Bu) (1.58 mmol) cooled at 0° C. was drop-wise treated under continuous stirring with cool CS$_2$ (1.58 mmol) and an aqueous solution (1 mL) of NaOH (1.60 mmol). When pH turned from 11 to 6 after ca. 2.5 h, the solution was slowly added under stirring to an aqueous cool (0° C.) solution (ca. 2 mL) of K[AuBr$_4$] (0.78 mmol), leading to the immediate precipitation of a reddish-brown solid that was filtered off, washed with water, and dried under reduced pressure with P$_2$O$_5$, the final yield being 81.2%.

Elemental analyses calculated for C$_{16}$H$_{28}$AuBr$_2$N$_3$O$_4$S$_2$: C, 25.71; H, 3.78; N, 5.62; S, 8.58%. Found: C, 25.79; H, 3.75; N, 5.48; S, 8.50%.

M.p.: decomposes at 161.7° C.

IR data (KBr, cm$^{-1}$): 3360 (v, N—H); 1735 (v, C=O ester); 1688 (v, C=O amide); 1561 (v, N—CSS); 1538 (v, amide II); 1252 (v, amide III); 1216 (v, C—O(t-Bu)); 1145 (v, (t-Bu)—O); 995, 545 (v$_{a,s}$, S—C—S); 383 (v$_{a,s}$, S—Au—S); 252, 222 (v$_{a,s}$, Br—Au—Br).

$^1$H NMR (300.13 MHz, acetone-D$_6$, 298 K): δ (ppm) 1.87 (C(CH$_3$)$_3$); 1.85-1.97 (C(CH$_3$)$_2$ Aib); 3.96, 4.00 (NCH$_3$); 5.15, 5.20 (CH$_2$ Sar); 7.83-8.41 (NH).

Example 9

[Au$^{III}$Cl$_2$((t-Bu)O-Aib$_2$-Sar-dtc)] (AUD14)

A water solution (ca. 3 mL) of HCl.H-Sar-Aib$_2$-O(t-Bu) (1.67 mmol) cooled at 0° C. was drop-wise treated under continuous stirring with cool CS$_2$ (1.68 mmol) and an aqueous solution (1 mL) of NaOH (1.67 mmol). When pH turned from 11 to 6 after ca. 2.5 h, the solution was slowly added under stirring to an aqueous cool (0° C.) solution (ca. 2 mL) of K[AuCl$_4$] (0.83 mmol), leading to the immediate precipitation of a dark-ochre solid that was filtered off, washed with water, and dried under reduced pressure with P$_2$O$_5$, the final yield being 76.3%.

Elemental analyses calculated for C$_{16}$H$_{28}$AuCl$_2$N$_3$O$_4$S$_2$: C, 29.19; H, 4.29; N, 6.38; S, 9.74%. Found: C, 29.02; H, 4.19; N, 6.48; S, 9.60%.

M.p.: decomposes at 166.9° C.

IR data (KBr, cm$^{-1}$): 3365 (v, N—H); 1733 (v, C=O ester); 1692 (v, C=O amide); 1563 (v, N—CSS); 1535 (v, amide II); 1252 (v, amide III); 1213 (v, C—O(t-Bu)); 1145 (v, (t-Bu)—O); 995, 546 (v$_{a,s}$, S—C—S); 384 (v$_{a,s}$, S—Au—S); 351 (v$_{a,s}$, Cl—Au—Cl).

$^1$H NMR (300.13 MHz, acetone-D$_6$, 298 K): δ (ppm) 1.87 (C(CH$_3$)$_3$); 1.85-1.98 (C(CH$_3$)$_2$ Aib); 4.00 (NCH$_3$); 5.18 (CH$_2$ Sar); 7.80-8.29 (NH).

Evaluation of Biological Activity

A—In Vitro

Preliminary in vitro cytotoxicity tests have been carried out for some of the example [Au$^{III}$X$_2$(pdtc)] complexes according to the invention.

Human prostate carcinoma PC3 cells (established from bone marrow metastasis and unresponsive to androgen treatment) were cultured in IMDM (Iscove's Modified Dulbecco's medium) supplemented with 10% heat-inactivated fetal bovine serum (FBS), penicillin (2 mg mL$^{-1}$), streptomycin (2 mg mL$^{-1}$), L-glutamine (0.1% w/v) at 37° C. in 5% CO$_2$ and moisture-enriched atmosphere.

Before use, [Au$^{III}$X$_2$(pdtc)] complexes (AUD6, AUD7, AUD8, AUD9) and cisplatin were dissolved in methyl sulfoxide (DMSO) just before the experiments. Calculated amounts of drug solutions were then added to the proper medium to a final concentration of 0.5% (v/v) DMSO which had no discernible effect on cell death. All the tested complexes were proved by 1H NMR studies, to be stable in DMSO over 48 h.

For the cytotoxicity assay, cells (2.5×10$^3$ cells mL$^{-1}$) were seeded in 96-well flat-bottomed microplates in IMDM supplemented with 10% heat-inactivated FBS and incubated at 37° C. in a 5% CO$_2$ atmosphere. The medium was then removed and replaced with a fresh one containing the compounds to be studied (previously dissolved in DMSO) at increasing concentrations (0.05-10 μM), thus exposing cells to the investigated compounds for 72 h. Triplicate cultures were established for each treatment. Cell viability was determined by a cell proliferation ELISA 5-bromo-2'-deoxyuridine colorimetric kit, according to the manufacturer's protocol. The percent cell viability was calculated by dividing the average absorbance of the cells treated with the tested compounds by that of the control, and plotted against drug concentration (logarithmic scale) to determine the IC$_{50}$ (drug concentration required to cause 50% cells growth inhibition relative to the control), the standard deviation being estimated from the average of three trials. For comparison purposes, the cytotoxicity of cisplatin was evaluated under the same experimental conditions.

As reported in table 1, exposure of PC3 cells to increasing concentrations of AUD6, AUD7, AUD8, AUD9 complexes resulted in a remarkable dose-dependent growth inhibition with IC$_{50}$ (the concentration of drug required to cause 50% growth inhibition) values, lower than the reference drug cisplatin, the most active being [Au$^{III}$Br$_2$((t-Bu)O-Aib-Sar-dtc)] (AU D8).

TABLE 1

Evaluation of in vitro cytotoxic activity ($IC_{50}$ ± S.D. [µM])
of the Au(III)-dithiocarbamato derivatives AUD6, AUD7, AUD8
and AUD9 toward human prostate carcinoma PC3 cells.

| Compound | $IC_{50}$ ± S.D. [µM] PC3 |
|---|---|
| AUD6 | 0.85 ± 0.07 |
| AUD7 | 1.0 ± 0.1 |
| AUD8 | 0.55 ± 0.05 |
| AUD9 | 0.75 ± 0.06 |
| cisplatin | 2.6 ± 0.2 |

The ability of the investigated compounds to induce apoptosis has been also investigated. One of the earliest features of apoptosis is a morphological change in the plasma membrane as a consequence of the translocation of the phospholipid phosphatidylserine (PS) membrane from the internal to the external layer of the cell membrane. In the presence of calcium ions, Annexin V has a high specificity and affinity for PS. Thus, the binding of Annexin V to cells with exposed PS provides a reliable and sensitive method to detect apoptosis. A population of apoptotic cells may contain necrotic cells binding Annexin V as well, due to their damaged plasma membrane. To distinguish between apoptotic and necrotic cells, the fluorescent dye propidium iodide (PI) is used since can cross damaged plasma membrane of necrotic cells only. Annexin-V binding and Propidium Iodide (PI) staining were detected by flow cytometry.

PC3 cells in exponential growth phase were incubated in IMDM supplemented with 10% heat-inactivated FBS either in presence or without the investigated compounds (5 µM) for 24 h. Cells were then harvested and resuspended in 100 µl of binding buffer (10 mM Hepes/NaOH pH 7.4, 140 mM NaCl, 2.5 mM $CaCl_2$), incubated with 5 µl of Annexin V-fluorescein isothiocyanate (FITC), and 10 µL of PI (10 µg/mL in binding buffer) in the dark for 15 min, and assayed after the addition of 0.3 µL binding buffer to each sample. Viable, Annexin V labeled cells were identified by flow cytometry according to their forward and right-angle scattering, electronically gated and analyzed on a FACScan flow cytometer.

Figure 1:
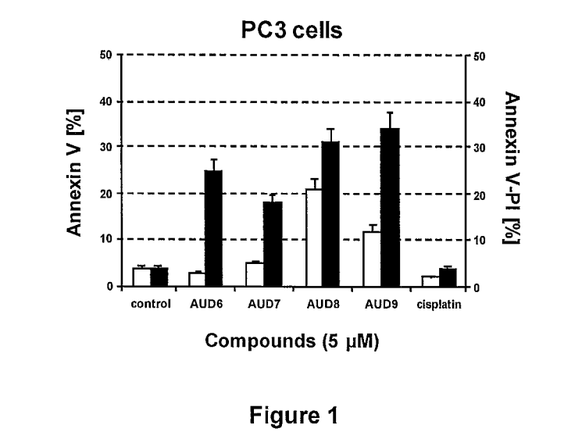
FIG. 1. Annexin V and Annexin V-PI analysis after treating human prostate carcinoma PC3 cells with some of the investigated Au(III)-dithiocarbamato complexes of the invention (5 μM) for 24 h. White bars: Annexin V (early apoptosis); black bars: Annexin V-PI (late apoptosis).

As clearly shown in FIG. 1, all the tested Au(III)-dithiocarbamate complexes are able to induce apoptosis, as evaluated by the marker of early apoptosis Annexin, inducing a significant increase of Annexin V binding/PI staining.

Figure 2:
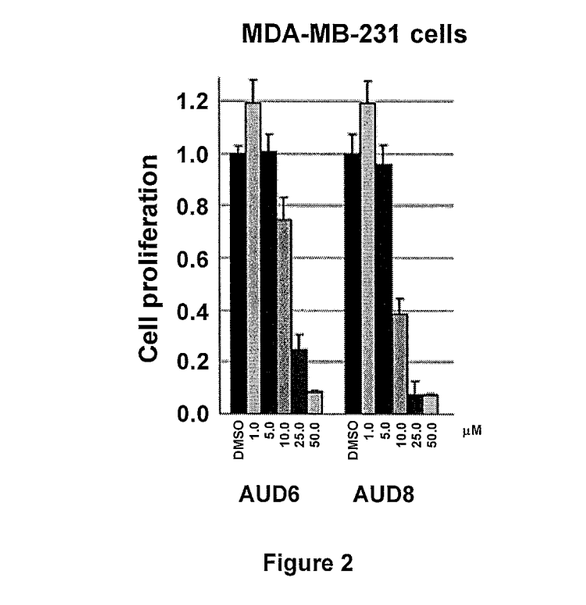
FIG. 2. Inhibitory effect of AUD6 and AUD8 on the proliferation of estrogen receptor α-negative human breast cancer MDA-MB-231 cells.

The growth-inhibitory effect of AUD6 and AUD8 on estrogen receptor α-negative human breast cancer MDA-MB-231 cells has been also evaluated. Cells were grown in RPMI 1640 medium supplemented with 10% heat-inactivated fetal bovine serum, penicillin (100 units $mL^{-1}$), streptomycin (100 µg $mL^{-1}$), L-glutamine (0.1% w/v) at 37° C. in 5% $CO_2$ and moisture-enriched atmosphere. For the cytotoxicity assay, cells were seeded in 96-well microplates in RPMI 1640 medium and grown to 70% to 80% confluency followed by addition of the compounds to be studied (previously dissolved in DMSO) at increasing concentrations (1-50 µM) and incubated at 37° C. in a 5% $CO_2$ atmosphere, thus exposing cells to the investigated compounds for 22 h. Triplicate cultures were established for each treatment. Cell respiration, as an indicator of cell viability, was determined by the mitochondrial-dependent reduction of MTT (3-(4,5-dimethylthiazol-2-yl)-2,5-diphenyltetrazolium bromide) to formazan as previously described [V. Milacic, D. Chen, L. Ronconi, K. R. Landis-Piwowar, D. Fregona, Q. P. Dou, Cancer Res. 2006, 66, 10478-10486]. Cell viability was calculated by dividing the average absorbance of the cells treated with the test compounds by that of the control, the standard deviation being estimated from the average of three trials. As reported in FIG. 2, AUD6 and AUD8 have similar inhibitory patterns, the latter showing slightly higher activity. Moreover, these results suggest that both compounds are similarly potent in inhibiting human breast cancer MDA-MB-231 cell growth as the previously investigated Au(III)-dithiocarbamato analogues [V. Milacic et al. 2006, ref. cit.].

Figure 3:
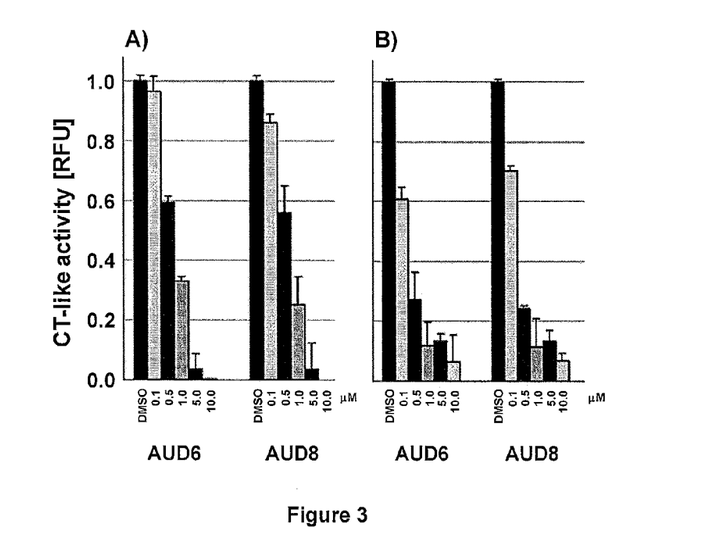
FIG. 3. Inhibition of proteasomal chymotrypsin-like activity induced by complexes AUD6 and AUD8 in A) purified rabbit 20S proteasome and B) MDA-MB-231 whole cell extract.

To investigate whether these compounds could also have the proteasome as a biological target, purified rabbit 20S proteasome (35 ng) or MDA-MB-231 whole cell extract (10 µg) were incubated with 20 µM of the substrate (for proteasomal chymotryptic (CT) activity) in 100 µL assay buffer (20 mmol $L^{-1}$ Tris-HCl (pH 7.5) in the presence of the compounds to be studied (previously dissolved in DMSO) at increasing concentrations (0.1-25 µM) or equivalent volume of neat DMSO as control. After 2 h incubation at 37° C., inhibition of each proteasomal chymotryptic activity was measured as previously described [V. Milacic et al. 2006, ref. cit.]. All the Au(III) complexes (AUD 6, AUD 8) were proved to inhibit the proteasomal chymotrypsin-like activity of both purified rabbit 20S proteasome (FIG. 3A) and MDA-MB-231 whole cell extract (FIG. 3B) in a concentration-dependent way resulting, again, two-fold more potent than the previously investigated Au(III)-dithiocarbamato analogues [V. Milacic et al. 2006, ref. cit.].

Further biological studies have been preliminarily showing that both investigated Au(III) complexes (AUD6, AUD8) induce accumulation of proteasome target proteins, such as Bax and p27, indicating that proteasome inhibition (associated with cell death) by AUD6 and AUD8 is functional and that the proteasome is a major cellular target.

B—In Vivo

Cell Culture and Cell Extract Preparation.

Estrogen receptor α-negative human breast cancer MDA-MB-231 cells were grown in RPMI 1640 medium supplemented with 10% fetal bovine serum, penicillin (100 units $mL^{-1}$), and streptomycin (100 µg $mL^{-1}$) at 37° C. in 5% $CO_2$ and moisture-enriched atmosphere.

Human Breast Tumor Xenograft Experiments.

Five week-old female athymic nude mice were purchased from Taconic Research Animal Services (Hudson) and housed according to protocols approved by the Institutional Laboratory Animal Care and Use Committee of Wayne State University. MDA-MB-231 cells ($5.0 \times 10^6$ cells $mL^{-1}$ suspended in 0.1 mL of serum-free RPMI 1640 medium) were inoculated subcutaneously (s.c.) in right flank of each mouse (four mice per group). When tumors reached the size of ca. 120 $mm^3$, mice were randomly grouped and treated daily with s.c. injection of either 1.0 mg $kg^{-1}$ of AUD6 or AUD8, or vehicle [10% DMSO, 20% Cremophore/ethanol (3:1) and 70% PBS]. Tumor size was measured every other day using calipers and their volumes were calculated according to the formula $width^2 \times length/2$. Mice have being treated for 13 days. Initial tumor growth inhibition was analyzed.

Figure 4:
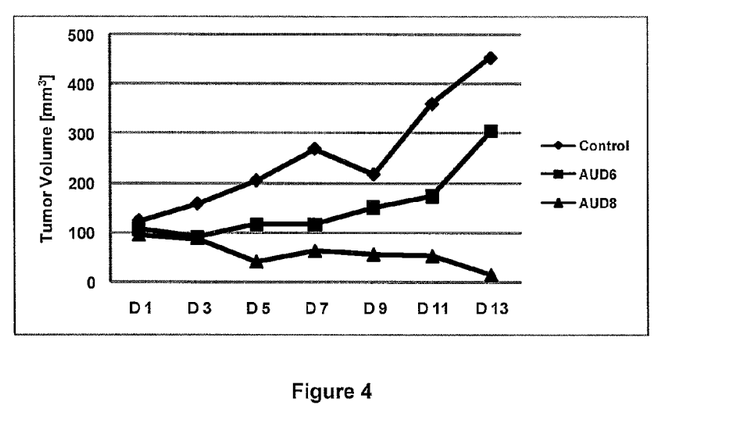
FIG. 4. In vivo inhibitory effect of AUD6 and AUD8 on human breast cancer xenografts. Female nude mice bearing with human breast cancer MDA-MB-231 cells were s.c. treated with 1 mg/kg gold complex AuD6 or AuD8 or control vector (V) daily.

The results obtained on the capability of both AUD6 and AUD8 complexes to inhibit the growth of human breast cancer (MDA-MB-231) xenografts in vivo are shown in FIG. 4. A significant tumor growth inhibition was observed after 13 days in tumor-bearing mice treated with AUD8. Control tumors grew to an average size of 453 $mm^3$, whereas AUD8-treated tumors grew to a much smaller average size, corresponding to >90% inhibition. Analogous treatment with AUD6 led to a moderate inhibition of tumor growth (ca. 33%). These results are consistent with the previously discussed in vitro studies, in which AUD8 was shown to be more potent than AUD6 in inhibiting MDA-MB-231 cells proliferation.

The invention claimed is:

1. An Au(III) complex [Au$^{III}$X$_2$(peptide/esterified peptide dithiocarbamato)], wherein X$_2$ and the peptide/esterified peptide dithiocarbamato moieties are the ligands, represented by the general formula (I)

and pharmaceutically acceptable salts thereof
wherein X$_2$ and the peptide/esterified peptide dithiocarbamato moieties are ligands and the ligands X$^1$, X$^2$, equal or different each other, are selected from the group consisting of Cl, Br, I, CN, SCN;
where Y is selected from O, S, NR$^7$, where R$^7$ is a residue selected from the group consisting of H, CH$_3$, straight or branched C$_2$-C$_6$ alkyl, C$_3$-C$_6$ cycloalkyl, phenyl; and R$^4$ is selected from the group consisting of H, CH$_3$, straight or branched C$_2$-C$_6$ alkyl, C$_3$-C$_6$ cycloalkyl, phenyl, (CH$_2$CH$_2$O)$_p$H where p is an integer comprised from 1 to 4; and
wherein the organic moiety [—(R$^1$)N—(R$^3$)(R$^2$)C—Z$_n$—(═O)C—] of the peptide/esterified peptide dithiocarbamato ligand is selected from the group consisting of -[Sar]-[Gly]-, -[Sar]-[Aib]- -[Sar]-[Phe]-, -[Sar]-[Ser]-, -[Sar]-[Aib]$_2$-, and -[Sar]-[Aib]$_3$-[Gly]-.

2. The Au(III) complex [Au$^{III}$X$_2$(peptide/esterified peptide dithiocarbamato)] according to claim 1, wherein the chiral carbon atom bound to R$^2$ and R$^3$ has R stereochemistry.

3. The Au(III) complex [Au$^{III}$X$_2$(peptide/esterified peptide dithiocarbamato)] according to claim 1, wherein the chiral carbon atom bound to R$^2$ and R$^3$ has S stereochemistry.

4. The Au(III) complex [Au$^{III}$X$_2$(peptide/esterified peptide dithiocarbamato)] according to claim 1, wherein X$^1$ and X$^2$ are a halogen selected from Cl and Br.

5. The Au(III) complex [Au$^{III}$X$_2$(peptide/esterified peptide dithiocarbamato)] according to claim 1, wherein Y of the peptide/esterified peptide dithiocarbamato ligand is O.

6. The Au(III) complex [Au$^{III}$X$_2$(peptide/esterified peptide dithiocarbamato)] according to claim 1, wherein R$^4$ of the peptide/esterified peptide dithiocarbamato ligand is selected from the group consisting of methyl, ethyl, t-butyl.

7. The Au(III) complex [Au$^{III}$X$_2$(peptide/esterified peptide dithiocarbamato)] according to claim 1 wherein:
the organic moiety [—(R$^1$)N—(R$^3$)(R$^2$)C—Z$_n$—(═O)C—]$_m$ of the peptide/esterified peptide dithiocarbamato ligand is selected from the group consisting of -[Sar]-[Gly]-, -[Sar]-[Aib]-, -[Sar]-[Ser]-, -[Sar]-[Aib]$_2$—, and -[Sar]-[Aib]$_3$-[Gly]-;
Y of the peptide/esterified peptide dithocarbamato ligand is O;
R$^4$ of the peptide/esterified peptide dithiocarbamato ligand is selected from the group consisting of methyl, ethyl, and t-butyl.

8. A method for treating neoplastic pathologies comprising the administration to a subject in need thereof an effective amount of an Au(III) complex defined in claim 1.

9. A composition comprising at least one of the Au(III) complex [Au$^{III}$X$_2$(peptide/esterified peptide dithiocarbamato)] according to claim 1 in combination with excipients and/or diluents pharmaceutically acceptable for treating neoplastic pathologies.

10. The method for preparing Au(III) complexes [Au$^{III}$X$_2$(peptide/esterified peptide dithiocarbamato)] according to claim 1 comprising at least the steps of:
a) in situ synthesis of the dithiocarbamato ligand by 1:1:1 stoichiometric reaction between a selected peptide or esterified peptide hydrochloride (p.HCl), carbon disulfide (CS$_2$) and a metal alkaline hydroxide (MOH, M=Na, K) in water at 0° C.;
b) [Au$^{III}$X$_2$(peptide/esterified peptide dithiocarbamato)] complex synthesis by coordination of the dithiocarbamato ligand to the Au(III) centre by a 2:1 ligand-to metal reaction between the dithiocarbamato ligand generated in situ to the previous step a) and M[Au$^{III}$X$_4$] (M=Na, K; X=Br, Cl) in a ratio 2:1 in water a 0° C.;
c) separation of the complex and optionally purification thereof.

* * * * *